(12) United States Patent
Zhang et al.

(10) Patent No.: US 7,789,851 B2
(45) Date of Patent: Sep. 7, 2010

(54) HEATING SOLUTIONS FOR FLUID MEDIA

(75) Inventors: Wenwei Zhang, Bellshill (GB); Vipin Pillai, Bellshill (GB); Frank Turnbull, Larkhall (GB)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 12/127,181

(22) Filed: May 27, 2008

(65) Prior Publication Data

US 2009/0299271 A1 Dec. 3, 2009

(51) Int. Cl.
*A61M 1/00* (2006.01)

(52) U.S. Cl. .................... 604/29; 392/393; 219/220; 219/553

(58) Field of Classification Search .................. 604/29; 392/393; 219/220, 552, 553
See application file for complete search history.

(56) References Cited

U.S. PATENT DOCUMENTS

| | | | | |
|---|---|---|---|---|
| 5,350,357 A | | 9/1994 | Kamen et al. ................ 604/29 |
| 5,493,629 A | * | 2/1996 | Stange ....................... 385/125 |
| 5,634,896 A | | 6/1997 | Bryant et al. ................ 604/29 |
| 5,938,634 A | | 8/1999 | Packard ....................... 604/29 |
| 5,989,423 A | | 11/1999 | Kamen et al. .............. 210/258 |
| 6,429,294 B1 | | 8/2002 | Masuda et al. ............. 530/362 |
| 6,595,948 B2 | | 7/2003 | Suzuki et al. ................ 604/29 |
| 6,613,095 B1 | | 9/2003 | Levin ...................... 623/23.65 |
| 6,656,227 B2 | | 12/2003 | Levin ...................... 623/23.65 |
| 7,153,285 B2 | | 12/2006 | Lauman et al. |
| D556,909 S | | 12/2007 | Reihanifam et al. ........ D24/169 |
| 7,458,951 B2 | | 3/2009 | Wardimon |
| 2002/0045851 A1 | | 4/2002 | Suzuki et al. ................ 604/28 |
| 2003/0220607 A1 | | 11/2003 | Busby et al. ................ 604/29 |
| 2006/0195064 A1 | | 8/2006 | Plahey et al. .............. 604/151 |
| 2007/0112297 A1 | | 5/2007 | Plahey et al. ............... 604/28 |
| 2008/0015492 A1 | | 1/2008 | Biesel ........................ 604/29 |
| 2008/0097283 A1 | | 4/2008 | Plahey ........................ 604/29 |
| 2009/0012450 A1 | * | 1/2009 | Shah et al. .................. 604/29 |

FOREIGN PATENT DOCUMENTS

WO WO 2008/027967 A1 3/2008
WO WO 2008/027971 A2 3/2008

* cited by examiner

*Primary Examiner*—Kevin C Sirmons
*Assistant Examiner*—Deanna K Hall
(74) *Attorney, Agent, or Firm*—Shumaker & Sieffert, P.A.

(57) ABSTRACT

A system and method for heating a fluid for delivery of the fluid in the context of a particular medical, pharmaceutical, industrial or mechanical application. A cassette is associated with an application, such as, for example, a peritoneal dialysis machine. The cassette includes one or more outlet tubes for delivery of the fluid to, for example, a patient. A heating device is associated with the cassette, and heats a portion of the fluid prior to delivery of the fluid to the patient, thereby saving time and electrical power during delivery of the fluid to the patient. Additionally, a controller can be employed to control the heating range of the heating device and thereby provide a temperature of the fluid that is adaptable to the patient or a particular application.

7 Claims, 6 Drawing Sheets

DOME PROFILE

HEATING SOLUTIONS FOR FLUID MEDIA

TECHNICAL FIELD

Embodiments are generally related to the heating of fluid media utilized in mechanical, pharmaceutical, industrial and medical applications. Embodiments are also related to techniques for the delivery of fluid to a patient. Embodiments are additionally related to dialysis equipment and related medical devices.

BACKGROUND OF THE INVENTION

Heated fluid flow continues to be crucial in achieving improved performance and efficiency in a broad range of mechanical, pharmaceutical, industrial processes and medical applications. In the pharmaceutical industry, for example, when a fluid having a solvent is blended with other active elements, accurate temperature control over the fluid is important for achieving quality drugs. A heater is not permitted to make direct contact with fluid because of pharmaceutical manufacturing processes. Similarly, in food and brewery process industries, temperature control is also necessary.

Furthermore, in medical applications, heated fluid flow is often used as a carrier of medicine to bring the medical element into a patient's body. Hemodialysis and peritoneal dialysis are two typical medical applications that require a heated fluid to be delivered to a patient. Peritoneal dialysis is an example of a medical application which requires the heating of the fluid. It can be appreciated, of course, that the use of peritoneal dialysis is not limited in this application.

Peritoneal dialysis is a method for removing waste, such as urea and potassium from the blood, as well as excess fluid, when the kidneys are incapable of this (i.e. in renal failure). The recent dialysis process employing peritoneal dialysis has been attracting attention because the cost of treatment is less expensive than with the dialysis process employing an artificial kidney and peritoneal adhesion can be prevented.

A peritoneal dialysis apparatus typically includes a fluid infusing bag connected to a fluid container (bag) containing a peritoneal fluid to be infused or delivered to a patient's peritonean (peritoneal cavity) and a reservoir bag connected to a drained fluid container (bag) for recovering the fluid drained from the patient. A pressure chamber, which accommodates the fluid infusing bag and reservoir bag, is formed in the housing of a dialysis apparatus or peritoneal dialysis apparatus. When the pressure in the pressure chamber is increased or decreased, the fluid infusing bag or reservoir bag pumps. The apparatus housing typically found in the art has a heater for heating the fluid in the fluid infusing bag held by the housing to a temperature within a predetermined temperature range.

Peritoneal dialysis is a form of renal dialysis, and is thus a renal replacement therapy. Because a patient's body can only adopt the fluid with a tight temperature range that is similar to that of a human body, the fluid must be heated prior to infusion to the abdominal cavity of a patient.

One example of a peritoneal dialysis machine is disclosed in U.S. Pat. No. 5,989,423, entitled "Disposable cassette, delivery set and system for peritoneal dialysis" which issued to Kamen et al. on Nov. 23, 1999 and is incorporated herein by reference. Such a device includes a disposable cassette for use in peritoneal dialysis that includes a pair of diaphragms, tube connectors, pump chambers, channel paths, and valves. In the configuration of U.S. Pat. No. 5,989,423, a disposable dialysate delivery set is provided for use in peritoneal dialysis and includes a cassette, multiple liquid flow paths, multiple valves, tube connectors, and disposable flexible plastic tubes to convey dialysate to and from the patient and other locations within the system. A system is also described for performing peritoneal dialysis includes disposable supply containers of fresh dialysate, a cassette including a pump, a disposable heater container, and conduits for carrying fresh dialysate and carrying heated dialysate.

Figure 1:
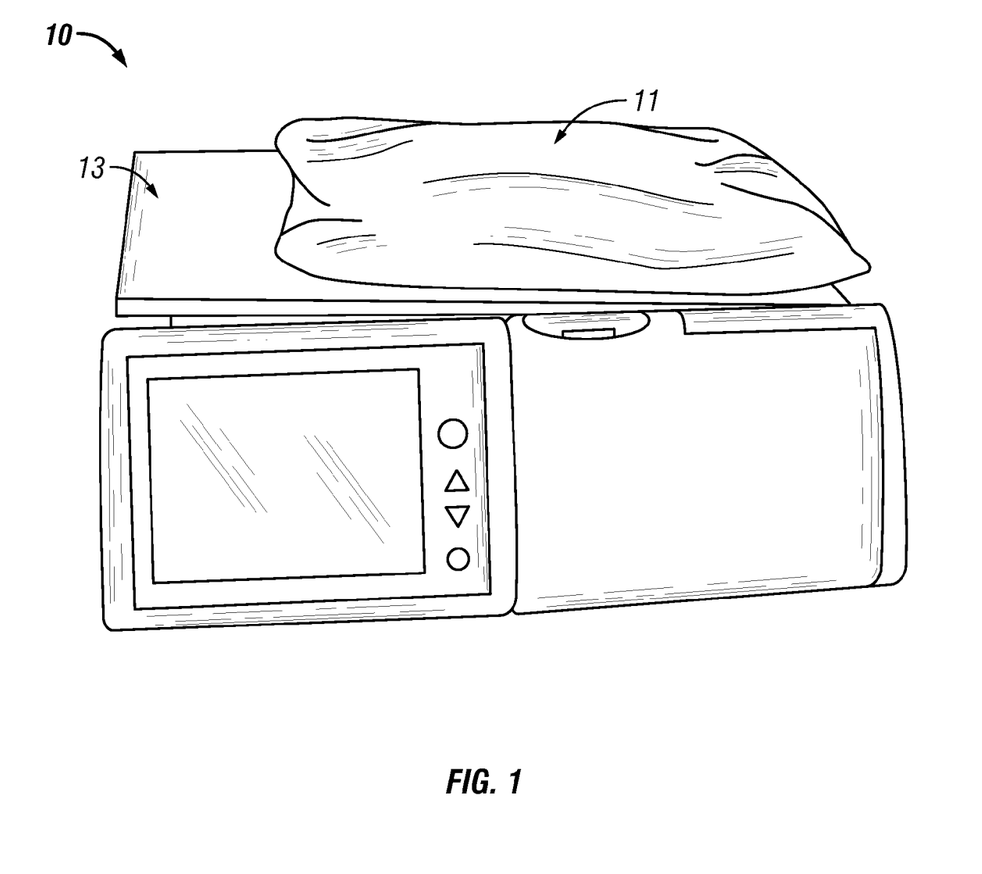
FIG. 1 illustrates a pictorial diagram of prior art heating system utilized in the context of a peritoneal dialysis machine.

The fluid of peritoneal dialysis is generally glucose or other contents dissolved in water with common strengths of around 0.5%, 1.5%, 2.5% and 4.25% respectively. Relying on gravity, the fluid from a fluid bag, such as bag 11 depicted in FIG. 1 is flowed to a disposable cassette, in which different active contents are mixed at a reservoir. The cassette is placed in a cassette machine 10 depicted in FIG. 1, and a pump within the machine 10 places pulsed pressure at the diaphragm side of the reservoir to push the fluid through the outlet of the cassette to the patient.

The cassette machine 10 shown in FIG. 1 is a prior art device for heating a fluid. Device 10 includes the use of a bag 11 containing fluid. The bag 11 is placed on a pan 13. The pan 13 is heated by a flexible heater (not shown) located on the back side of the pan 13. Thus, the whole bag 11 of fluid is heated before the fluid flows into a disposable cassette (not shown) located within a dialysis machine. Such an approach presents a straightforward solution for heating the fluid; however, it has its drawbacks.

First, the heating system including the pan is quite bulky especially for applications at patients' home. Second, this type of approach is less efficiency because it has to heat up all the fluid in the bag rather than the portion of the fluid that will go to the abdomen of patient directly. Thus, the system approach depicted in FIG. 1 requires a long warm-up time, high electrical power and a large heating system to maintain the temperature of the whole bag of fluid. Third, in such an approach, it is difficult to accurately control the temperature of fluid infused into the abdomen of the patient due to a long path of the heated fluid delivered from the bag to the patient, which may cause the temperature of the heated fluid out of the range requested.

Given those disadvantages, it is believed that several solutions can be developed to overcome the aforementioned issues associated conventional heating methods.

BRIEF SUMMARY

The following summary is provided to facilitate an understanding of some of the innovative features unique to the embodiments disclosed and is not intended to be a full description. A full appreciation of the various aspects of the embodiments can be gained by taking the entire specification, claims, drawings, and abstract as a whole.

It is, therefore, one aspect of the present invention to provide for an improved system and method for the heating of fluid to be delivered for a particular medical, pharmaceutical, industrial or other mechanical application.

It is another aspect of the present invention to provide for an improved system and method for heating fluid for delivery to a medical application, such, as for example, a dialysis system.

It is another aspect of the present invention to provide for an improved solution for heating fluid for delivery to a patient.

The aforementioned aspects and other objectives and advantages can now be achieved as described herein. A system is disclosed for heating a fluid for delivery to a particular application, such as, for example, a patient via a peritoneal dialysis machine. In general, a cassette is associated with a particular application, such as, for example, a peritoneal dialysis machine. The cassette includes one or more outlet tubes for delivery of the fluid to a patient. A heating device is associated with the cassette, and heats a portion of the fluid prior to delivery of the fluid to the patient, thereby saving time and electrical power during delivery of the fluid to the patient. Additionally, a controller is employed to control the heating range of the heating device and thereby provide a temperature of the fluid that is adaptable to the patient.

In one possible embodiment, the heating device may be a light source, such as, for example, an invisible infrared and/or UV light source which could be, for example, a laser, LED or a light bulb or an array of such components, for heating the fluid. In such a situation, an optical adapter may be associated with the light source, and serves to increase the efficiency of heating the fluid. An optical fiber can also be provided, such that the light (e.g., infrared or UV light) is delivered through the optical fiber to a particular zone of the cassette to heat the fluid. Alternatively, the light can be delivered through the optical fiber to the one or more of the outlet tubes associated with the cassette to heat the fluid.

In another embodiment, the heating device can be provided in the form of a microwave enclosure that heats up the fluid within the cassette or at the outlet tube(s) associated with the cassette. In still another embodiment, the heating device can be provided as an ultrasonic device that heats up the fluid within the cassette or at the outlet tube(s).

In another embodiment, a mini-pan bonded with a flex heater can be mounted on a cassette machine associated with the cassette in order to heat the fluid in the cassette. In still another embodiment, one or more cylinder heater dampers can be provided for heating the fluid in the outlet tube(s) of the cassette. Additionally, the heating device may be implemented as a resistive ink printed at a reservoir area of the cassette in order to heat the dialysis area in the reservoir area of the cassette. The resistive print ink printed at the reservoir area of the cassette can be utilized to heat the fluid in the reservoir area of the cassette either from the dome side or from the diaphragm side. Alternatively, the heating device may include a printing resistive film attached to the cassette. Such a printing resistive film can be attached at the cassette without a pan and function as the heating media.

BRIEF DESCRIPTION OF THE DRAWINGS

The accompanying figures, in which like reference numerals refer to identical or functionally-similar elements throughout the separate views and which are incorporated in and form a part of the specification, further illustrate the embodiments and, together with the detailed description, serve to explain the embodiments disclosed herein.

DETAILED DESCRIPTION

The particular values and configurations discussed in these non-limiting examples can be varied and are cited merely to illustrate at least one embodiment and are not intended to limit the scope thereof.

Several approaches can be utilized to solve the problems associated with prior art heating techniques in the context of the delivery of heated fluid to a particular application, such as, for example (but not limited to) peritoneal dialysis. Note that the discussion of peritoneal dialysis as provided herein represents merely one possible application for the heating and delivery of fluid. Other applications, including pharmaceutical, industrial and other mechanical applications can also utilize the novel solutions to heating fluid described herein. Peritoneal dialysis and related dialysis machinery is discussed herein for general illustrative and edification purposes only.

The first approach involves the use of an invisible light source (e.g., infrared/ultraviolet) to heat up fluid in a cassette or in the outlet tube of the cassette utilized in a peritoneal dialysis machine/system.

Figure 2:
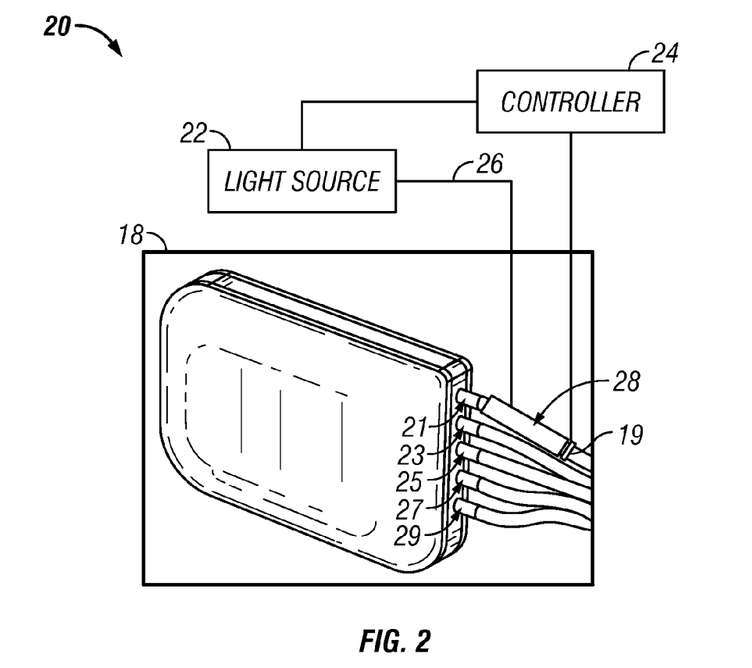
FIG. 2 illustrates a schematic diagram depicting a system that includes the use of an infrared/ultraviolet light source to heat up fluid at the outlet of a tube in the context of a peritoneal dialysis machine, in accordance with a preferred embodiment.

Water fluid itself has strong absorption at invisible IR and UV wavelengths. The first approach described herein can involve the use of, for example, an invisible infrared/ultraviolet light source system to focus on the fluid at the outlet of the cassette to heat up the fluid through its absorption at the selected wavelength. Light source 22 may be for example, a laser, a light bulb or even an LED, or an array of such components, depending upon design considerations.

FIG. 2 illustrates a schematic diagram depicting a system 20 that includes the use of a cassette 18 in association with a light source 22 such as, for example, an infrared/ultraviolet light source, that can be utilized to heat a fluid at the outlet of a tube 21 in the context of a peritoneal dialysis machine, in accordance with a preferred embodiments. As indicated previously, the light source 22 may be, for example, an infrared light source, a UV light source, and/or, for example, a light bulb, an LED or a laser, or array of those or a combination thereof, depending upon design considerations and goals. The configuration depicted in FIG. 2 illustrates a peritoneal dialysis concept involving the use of an invisible light source 22 (e.g., an infrared and/or UV light source) utilized to heat the fluid at the outlet of the tube 21 prior to the delivery of the fluid to a patient in the context of a dialysis machine/system. A light beam can be provided via the light source 22 and travels through an optical fiber 26 for delivery to a light coupler 28 or adapter, which is mounted at the outlet tube 21 of the cassette 18. The purposes of the adapter or light coupler 28 are to couple and focus the light at the fluid in the outlet tube 21, and reflect the light forward and backward within the adaptor/light coupler 28 until the energy of the light is totally absorbed by the fluid. A temperature sensor 19 can be applied to sense the temperature of the fluid, thereby permitting feedback to control the intensity of the invisible light source 22 (e.g., IR or UV) to close-loop control the temperature of the fluid. A controller 24 is electrically connected to the light source 22 and the temperature sensor 18 to assist in providing such feedback. Note that one or more other outlet tubes 23, 25, 27 and 29 can be provided with respect to cassette 18. Such tubes 23, 25, 27 and 29 may also be provide with a similar configuration as that of outlet tube 21, depending upon design considerations and goals.

Figure 3:
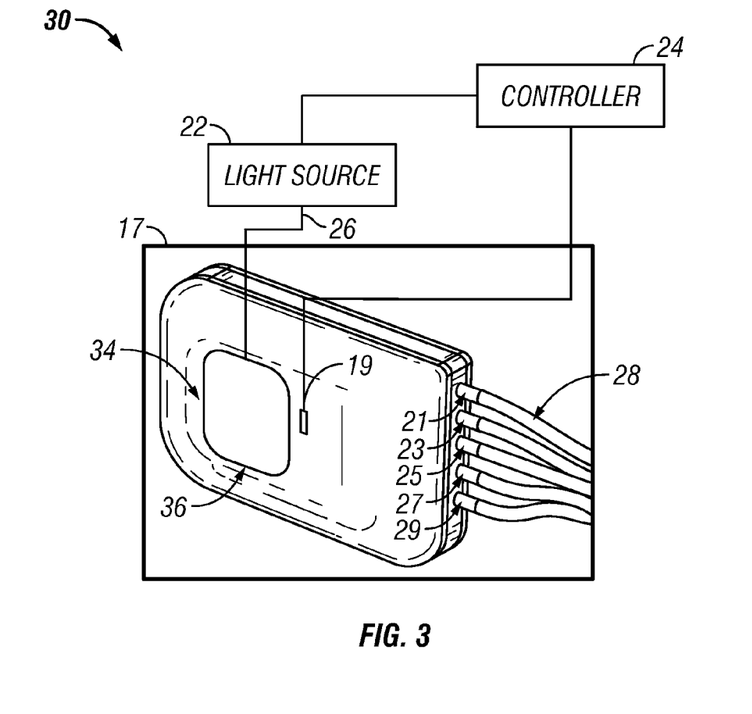
FIG. 3 illustrates a schematic diagram depicting a system in which light beam is focused at the fluid in a reservoir of a cassette through an adapter for use with a peritoneal dialysis machine, in accordance with an alternative embodiment.

FIG. 3 illustrates a schematic diagram depicting a system 30 in which light beam is focused at the fluid in a reservoir of a cassette through an adapter for use with a peritoneal dialysis machine, in accordance with an alternative embodiment. Note that in FIGS. 2-3, identical or similar parts or elements are generally indicated by identical reference numerals. System 30 thus represents an alternative to the system 20 depicted in FIG. 2. In the configuration depicted in FIG. 3, an alternative embodiment is thus illustrated with respect to the first approach described above. In the system 30 shown in FIG. 3, light beam can be provided by a light source 22 and focused at the fluid in a reservoir 34 of the cassette 17 through an adapter or light coupler 36. A temperature sensor 19 can also be applied to feedback control temperature through a light source intensity controller 24. In the configuration depicted in FIG. 3, the optical fiber 26 connects light source 22 with the light coupler 36. The controller 24 is electrically connected to the temperature sensor 19 and the light source 22.

The second approach for overcoming the problems associated with the prior art techniques described earlier involves the use of microwave radiation to heat up fluid in a cassette. Water fluid itself has strong absorption at a certain frequency (e.g., 2.45 GHz) of microwave radiation. The second approach described herein develops a microwave enclosure to heat up the fluid. Since the selected frequency of 2.45 GHz microwave only heats the water fluid rather than other materials around the cassette, it leaves the cassette or the outlet tube unheated.

Figure 4:
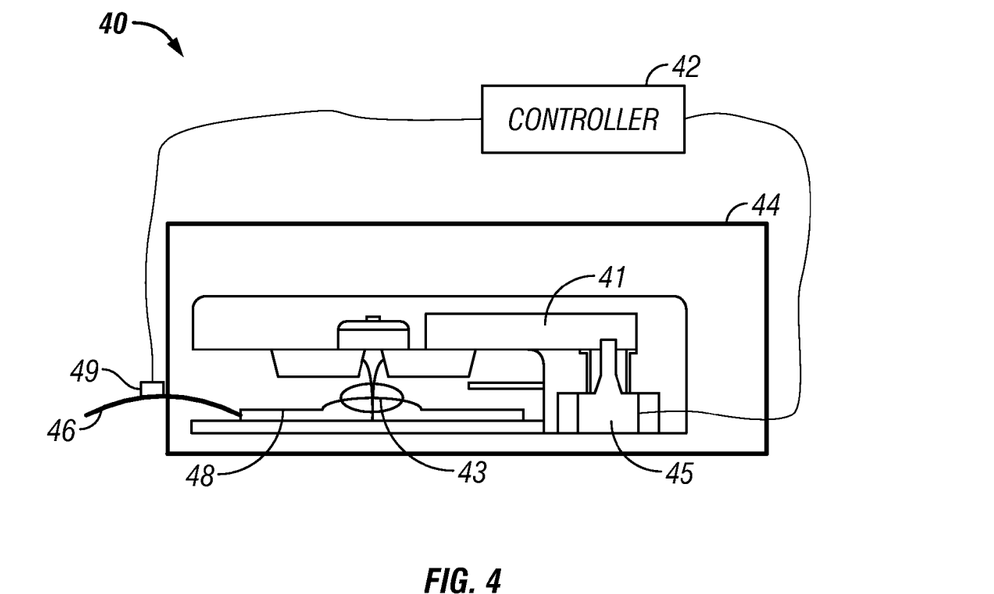
FIG. 4 illustrates a schematic diagram of a system that includes the use of a microwave enclosure mounted into the cave of a cassette machine to heat up the reservoir of the case for use with a peritoneal dialysis machine, in accordance with an alternative embodiment.

FIG. 4 illustrates a schematic diagram of a system 40 that includes the use of a microwave enclosure mounted into a cave 44 of a cassette machine to heat up a reservoir of the case for use with a peritoneal dialysis machine, in accordance with an alternative embodiment. System 40 generally includes a controller 42 that is electrically connected to a temperature sensor 49 that in turn is located proximate to an outlet tube 46. System 40 includes a cassette 48 and a heating area 43 in the cassette 48. A waveguide 41 is also provided with respect to a magnetron 45. The controller 42 is also electrically connected to the magnetron 45. In the configuration depicted in FIG. 4, the temperature sensor 49 is applied at the outlet of the tube 46 to feedback control the microwave power, thereby accurately controlling the temperature of the fluid. In this scenario, the magnetron 45 generates the microwave, which is guided to the reservoir of the cassette 48.

Figure 5:
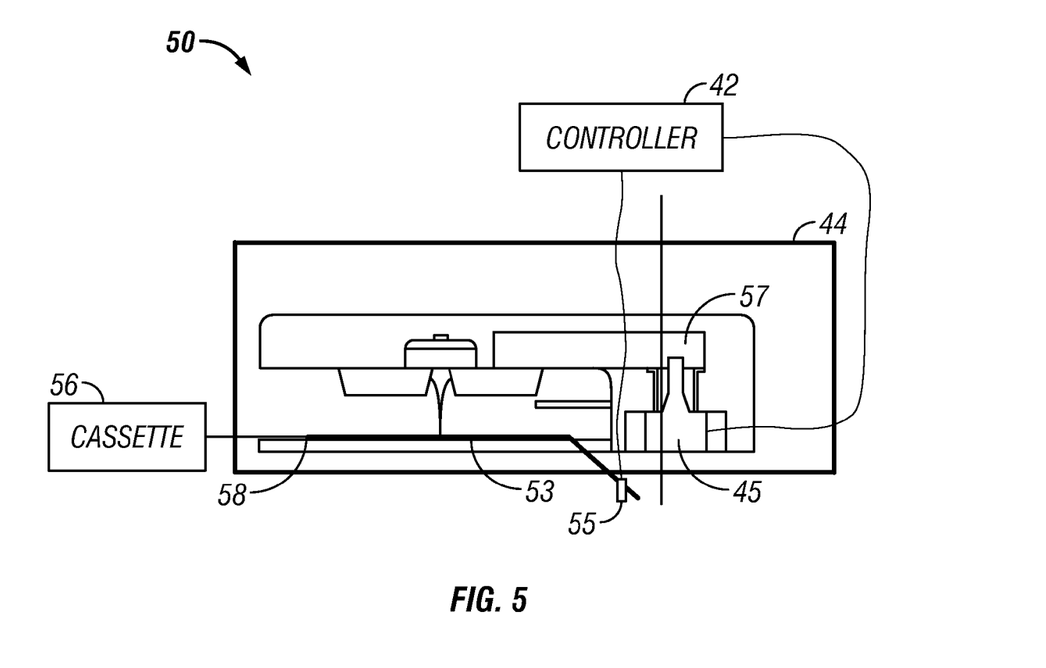
FIG. 5 illustrates a schematic diagram of a system that includes a microwave enclosure focused on an outlet tube to hear fluid prior to the delivery of the fluid to a patient, in accordance with an alternative embodiment.

FIG. 5 illustrates a schematic diagram of a system 50 that includes a microwave enclosure focused on an outlet tube 58 to heat a fluid prior to the delivery of the fluid to a patient, in accordance with an alternative embodiment. Note that in FIGS. 4-5, identical or similar parts or elements are generally indicated by identical reference numerals. The configuration depicted in FIG. 5 thus represents an alternative implementation of the configuration depicted in FIG. 4. System 50 generally includes a controller 42 that is electrically connected to a temperature sensor 55 and a magnetron 45. A cave 44 can be provided within the context of the overall cassette machine. A cassette 56 is depicted in FIG. 5 external to the cave 44. The cassette 56 is, however, electrically connected to the outlet tube 58. A heating area 53 is also depicted in FIG. 5 as maintained within cave 44. The configuration of system 50 thus illustrates a concept involving the use of a microwave enclosure to heat up fluid at the outlets of the cassette 56. In FIG. 5, the microwave enclosure is focused on the outlet tube 58 to heat the fluid prior to delivery of the fluid to a patient.

Figure 6:
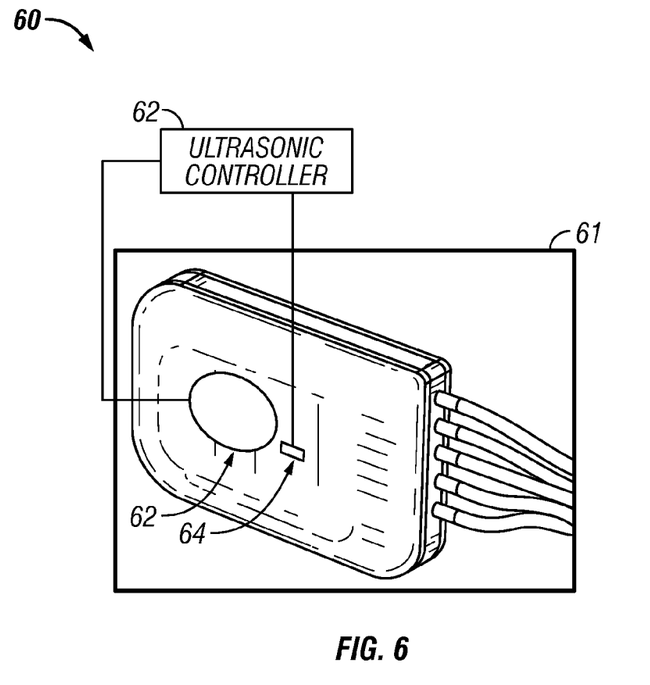
FIG. 6 illustrates a pictorial diagram of an ultrasonic device for heating up fluid in a cassette for use with a peritoneal dialysis machine, in accordance with an alternative embodiment.

FIG. 6 illustrates a pictorial diagram of a system 60 that includes the use of an ultrasonic device for heating fluid in a cassette 61 for use with a peritoneal dialysis machine, in accordance with an alternative embodiment. System 60 generally includes the use of an ultrasonic controller 62 that is electrically connected to an ultrasonic actuator 62. A temperature sensor 64 is also electrically connected to the ultrasonic controller 62. In the configuration depicted in FIG. 6, a high intensity focused ultrasonic transducer/actuator 62 generates focused ultrasonic waves at the fluid at the reservoir of the cassette 61. The temperature sensor 64 can be applied at the outlet of the tube to feedback control the microwave power, thereby accurately controlling the heated temperature of the fluid.

Figure 7:
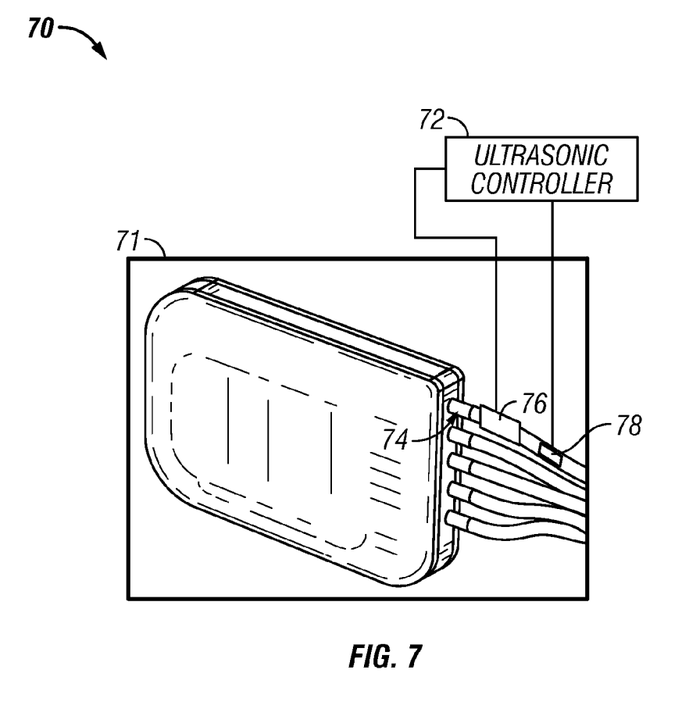
FIG. 7 illustrates a pictorial diagram of an ultrasonic device utilized heat up fluid in an outlet tube of a cassette fluid for use with a peritoneal dialysis machine, in accordance with an alternative embodiment.

FIG. 7 illustrates a pictorial diagram of a system 70 that includes the use of an ultrasonic device utilized for heating fluid in an outlet tube of a cassette 71 for use with a peritoneal dialysis machine, in accordance with an alternative embodiment. The configuration depicted in FIG. 7 represents an alternative version of the configuration depicted in FIG. 6. System 70 generally includes an ultrasonic controller 72 that is electrically connected to a temperatures sensor 78 and an ultrasonic transducer 76. The system 70 thus utilizes an ultrasonic device (i.e., ultrasonic controller 72 and ultrasonic transducer 76) to generate focused ultrasonic waves at the outlet tube 74 to heat the fluid prior to delivery of the fluid to a patient.

Figure 8A:
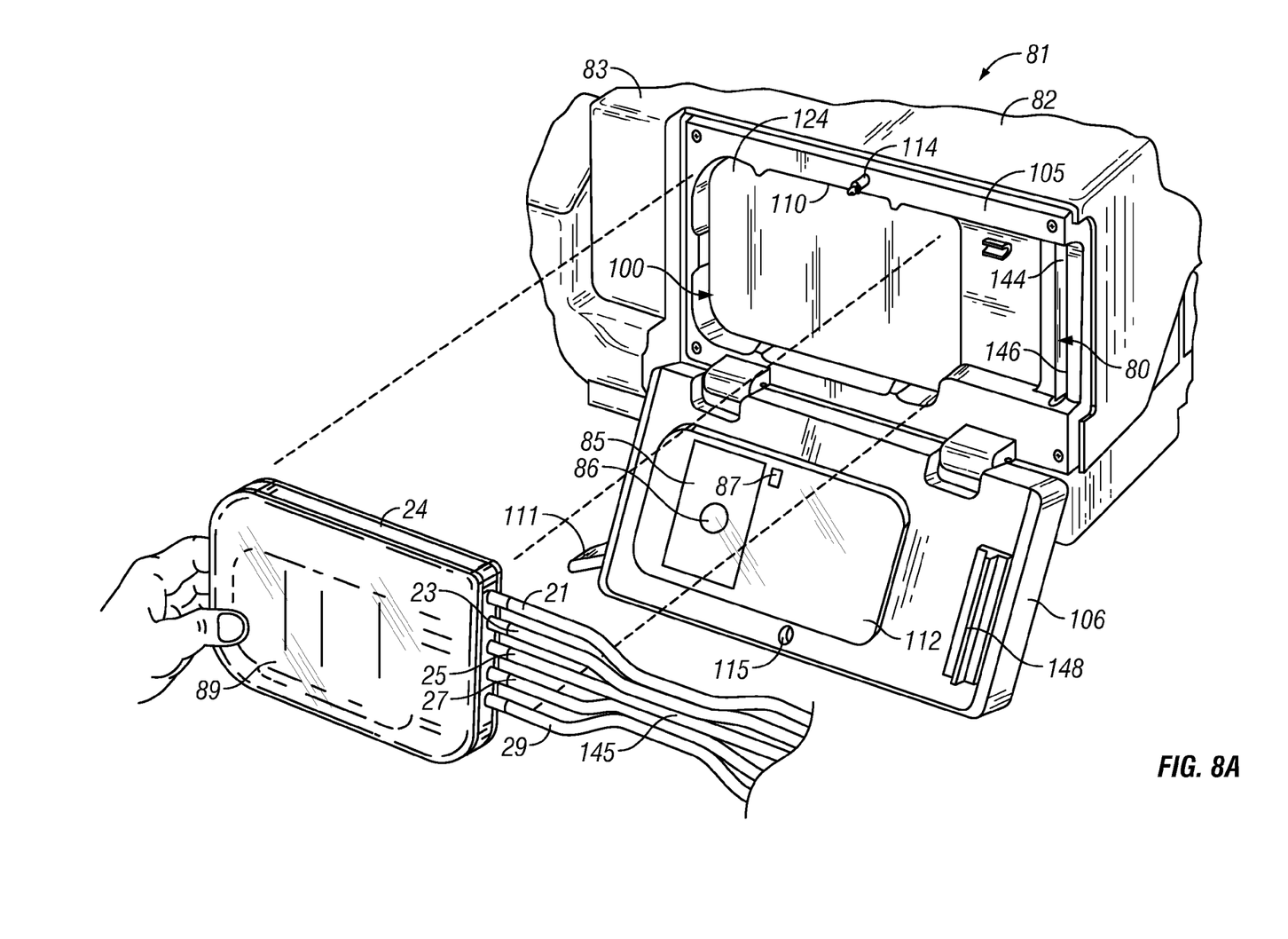
FIG. 8(a) illustrates a pictorial diagram of a mini pan bonded with a flex heater in a cassette machine in accordance with an alternative embodiment.

FIG. 8(a) illustrates a pictorial diagram of a system 81 that includes the use of a mini pan bonded with a flex heater in a cassette machine 83 in accordance with an alternative embodiment. The system 81 generally includes a cassette machine 83 that includes a housing 82 and the use of a door 106 that opens and closes with respect to the cassette machine 83. The door 106 is generally hinged to a front plate 105. Additionally, a door latch 115 can be provided, which is capable of being operated by a latch handle 111 that contacts a latch pin 114 when the door 106 is closed. Moving the latch handle 111 downward when the door 106 is closed engages the latch 115 to the pin 114 to lock the door 106. Moving the latch handle 111 upward when the door 106 is closed releases the latch 115 from the pin 114. This allows the door 106 to be opened to gain access to the interior of the holder 100.

The door 106 includes the use of an occluder blade 144 that extends through a slot 146 in a plate 105 of the holder 100. When the holder door 106 is closed, the blade 144 faces an elongated occluder bar 148 carried on the holder door 106. A gasket 112 is also incorporated into door 106 and can maintain a mini-pad 85 having a flex heater 86. A temperature sensor 87 can be located proximate to the mini-pad 85. A cassette 24 includes dome side 89 and a plurality of flexible outlet tubes 21, 23, 25, 27, 29. A tube region 145 of the flexible tubing 21, 23, 25, 27, and 29 is held in a mutually close relationship near the cassette 24. Note that a liquid shutoff assembly 80, which forms a part of a pneumatic actuator module, can serve to block all liquid flow through the cassette 24 in the event of a power failure or another designated error condition.

An integral elastomeric membrane 124 may also be provided in some embodiments. In system 81, when a cassette such as cassette 24 is sitting in the machine 83, the area of cassette 24 is contacted with the mini pan 85, and thus the fluid is heated. The temperature sensor 87 is applied to feedback control the temperature through a controller such as the controllers illustrated and described herein.

Figure 8B:
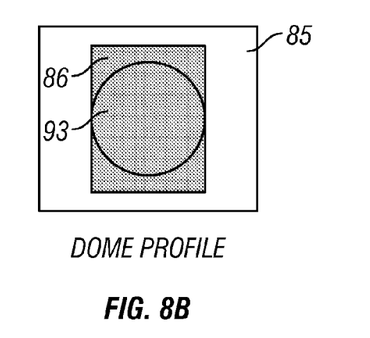
FIG. 8(b) illustrates a schematic diagram depicting the configuration of a mini pan in accordance with an alternative embodiment.

FIG. 8(b) illustrates a schematic diagram depicting the configuration of a mini pan 85 in accordance with an alternative embodiment. In the configuration depicted in FIG. 8(b), the flex heater 86 can be disposed on the dome side 89 (see FIG. 8(a)) of the cassette 24. The dome profile 93 is also depicted in FIG. 8(b).

Figure 9A:
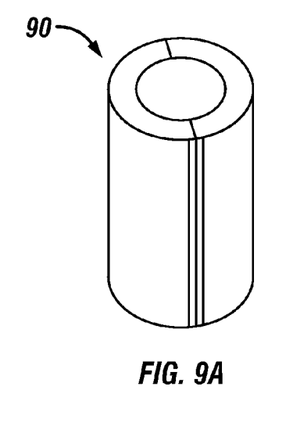
FIG. 9(a) illustrates a pictorial diagram of flex heaters that can be adapted for use in accordance with an alternative embodiment.
Figure 9B:
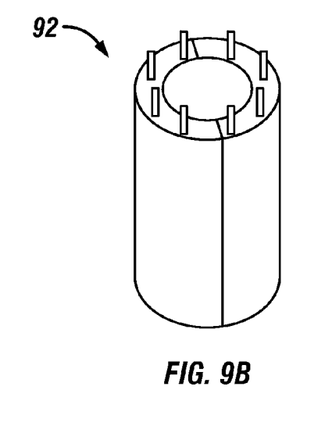
FIG. 9(b) illustrates a pictorial diagram of cartridge heaters that can be adapted for use in accordance with an alternative embodiment.

FIG. 9(a) illustrates a pictorial diagram of flex heaters 90 that can be adapted for use in accordance with an alternative embodiment. FIG. 9(b) illustrates a pictorial diagram of cartridge heaters 92 that can be adapted for use in accordance with an alternative embodiment. Two half-cylinder heater dampers can be bolted around an outlet tube to heat the fluid at the outlet tube. The dampers can be heated by the flex heaters shown in FIG. 9(a) or cartridge heaters shown in FIG. 9(b).

Figure 9C:
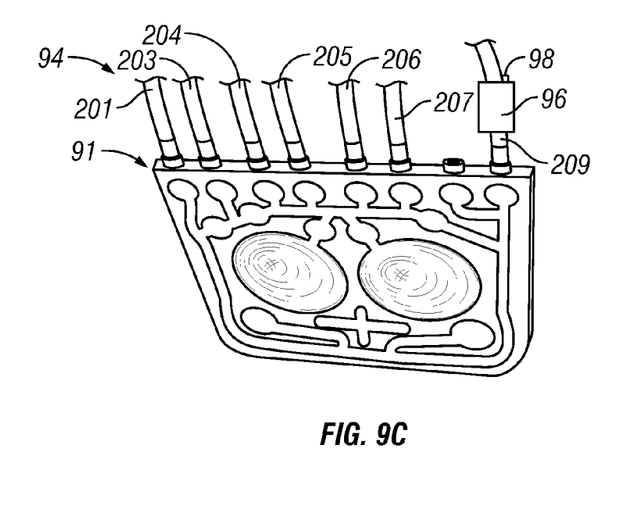
FIG. 9(c) illustrates a schematic diagram depicting a technique for clamping the heater at the outlet tube of the cassette in accordance with an alternative embodiment.

FIG. 9(c) illustrates a schematic diagram depicting a system 94 for clamping a heater at an outlet tube 209 of a cassette 91 in accordance with an alternative embodiment. Cassette 91 can be connected to a plurality of flexible tubes 201, 203, 204, 205, 206, 207, and 209. A heater damper 96 is shown clamped about tube 209. A temperature sensor is disposed next to the heater damper 96 and the tube 209.

Other solutions are possible. For example, another solution is to directly print the conductive ink on the reservoir area at either the dome side or the diaphragm side. During manufacturing of cassette, resistive ink can be printed on the cassette to directly heat up the dedicated on the cassette, thus heating up the fluid precisely. A thermistor can be mounted near the heated area to monitor the temperature and feedback control the heating power of the printing ink.

Another solution involves the use of a printing resistive film to heat fluid in the cassette. As compared with a conventional wire-wound, etched foil flex heater and even transparency heater (e.g., ITO based); this approach may utilize two types of heaters based on printing a thick film resistive heating element. A first approach involves the use of a resistive element, which can be may be printed on a rigid substrate. In such a scenario, the substrate can be configured from a thermally conductive but electrically isolated material such as aluminum with an electrical isolation coating. Then, the resistive element can be printed on the coating. Thereafter, the fluid in the cassette will be heated through the substrate when the cassette is in contact with the substrate. The substrate may also be configured from a thermally isolated material such as nylon and/or polycarbonate. In this situation the resistive element printed on the substrate will directly make contact with the cassette to heat the fluid therein. Here, the substrate can function as a thermal isolator to avoid thermal loss to other places.

The second approach involves printing the resistive element on flex tape. Furthermore, the substrate can be printed on an adhesive tape, rolling in a roll. When requested, flex tape can be self-adhesively attached to the cassette to heat the fluid within the cassette.

It will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A system for heating a fluid flowing through a fluid delivery cassette managed within a housing to a patient, said system comprising:
   a fluid delivery housing for accepting and controlling functions of a fluid delivery cassette;
   a fluid delivery cassette including at least one outlet tube extending from said fluid delivery cassette and a pump, said fluid delivery cassette used for delivery of said fluid to said patient;
   a heating device included with said fluid delivery cassette, wherein said heating device comprises a light source with invisible wavelength, an optical fiber and a light coupler, wherein light from said light source is delivered through said optical fiber to said light coupler which reflects light from the light source forward and backward within the light coupler to transfer energy from the light to said fluid, which flows through said light coupler to heat said fluid prior to delivery of said fluid to said patient, and
   a controller and a heat sensor controlling heating range of at least one of said heating device and said fluid to provide a temperature of said fluid that is comfortable to said patient.

2. The system of claim 1 wherein said light source comprises at least one invisible infrared light source.

3. The system of claim 1 wherein said light source comprises at least one UV light source.

4. The system of claim 1 wherein said light source is delivered through said optical fiber to said cassette to heat said fluid.

5. The system of claim 1 wherein said light coupler is mounted at said outlet tube of said cassette.

6. A system for heating a fluid, said system comprising:
   a fluid delivery cassette having at least one outlet tube for delivery of said fluid to a particular application;
   a heating device included with said fluid delivery cassette, wherein said heating device comprises a light source with invisible wavelength, an optical fiber and a light coupler, wherein light from said light source is delivered through said optical fiber to said light coupler which reflects light from the light source forward and backward within the light coupler to transfer energy from the light to said fluid, which flows through said light coupler to heat a portion of said fluid prior to delivery of said fluid to said particular application, thereby saving time and electrical power during said delivery of said fluid;
   a fluid delivery housing for accepting said cassette and controlling functions of a fluid delivery cassette and said heating device; and a controller that controls a heating range of said heating device and providing a temperature to said fluid for said particular application.

7. A method for heating a fluid, said method comprising:

providing a fluid delivery cassette having at least one outlet tube extending therefrom for delivery of said fluid to a patient;

associating a heating device comprising a light source with invisible wavelength using an optical fiber and a light coupler which reflects light from the light source forward and backward within the light coupler to transfer energy from the light to said fluid, which flows through said light coupler to heat said fluid within at least one of said fluid delivery cassette and said at least one outlet tube, wherein said light source heats a portion of said fluid prior to delivery of said fluid to said patient from said fluid delivery cassette, and utilizing a controller to control temperature of said heating device and said fluid and also flow of said fluid to said patient.

* * * * *